United States Patent
Akutsu et al.

(10) Patent No.: US 10,702,472 B2
(45) Date of Patent: Jul. 7, 2020

(54) PRODUCTION METHOD OF EDIBLE SUSTAINED-RELEASE FUNCTIONAL MATERIAL AND EDIBLE SUSTAINED-RELEASE FUNCTIONAL MATERIAL

(71) Applicants: AOBAKASEI KABUSHIKI KAISHA, Sendai-shi, Miyagi (JP); TOHOKU TECHNO ARCH CO., LTD., Sendai-shi, Miyagi (JP)

(72) Inventors: Mitsuaki Akutsu, Sendai (JP); Shunsuke Matsumoto, Sendai (JP); Teruo Miyazawa, Sendai (JP); Kiyotaka Nakagawa, Sendai (JP); Shigeta Aoki, Sendai (JP); Junya Ito, Sendai (JP); Taiki Shiomi, Sendai (JP)

(73) Assignees: AOBAKASEI KABUSHIKI KAISHA, Sendai-shi (JP); TOHOKU TECHNO ARCH CO., LTD., Sendai-shi (JP)

( * ) Notice: Subject to any disclaimer, the term of this patent is extended or adjusted under 35 U.S.C. 154(b) by 0 days.

(21) Appl. No.: 16/145,414

(22) Filed: Sep. 28, 2018

(65) Prior Publication Data

US 2019/0105266 A1 Apr. 11, 2019

(30) Foreign Application Priority Data

Oct. 6, 2017 (JP) ................. 2017-195554

(51) Int. Cl.

| | | |
|---|---|---|
| A61K 36/00 | (2006.01) |
| A61K 9/00 | (2006.01) |
| A61K 47/36 | (2006.01) |
| A61K 47/02 | (2006.01) |
| A61K 47/44 | (2017.01) |
| A61K 47/42 | (2017.01) |
| A61K 31/122 | (2006.01) |
| A61K 31/047 | (2006.01) |
| A61K 36/185 | (2006.01) |
| A61K 36/55 | (2006.01) |
| A61K 31/336 | (2006.01) |
| A23L 33/115 | (2016.01) |
| A23L 29/281 | (2016.01) |
| A23L 29/10 | (2016.01) |
| A23L 29/00 | (2016.01) |
| A23L 33/125 | (2016.01) |
| A61K 35/60 | (2006.01) |
| A23L 29/20 | (2016.01) |
| A23D 9/05 | (2006.01) |
| A23L 33/10 | (2016.01) |
| A23L 29/30 | (2016.01) |
| A23D 9/007 | (2006.01) |
| A23L 33/12 | (2016.01) |
| A23L 33/105 | (2016.01) |

(52) U.S. Cl.
CPC ............ *A61K 9/0056* (2013.01); *A23D 9/007* (2013.01); *A23D 9/05* (2013.01); *A23L 29/04* (2016.08); *A23L 29/06* (2016.08); *A23L 29/10* (2016.08); *A23L 29/20* (2016.08); *A23L 29/284* (2016.08); *A23L 29/30* (2016.08); *A23L 33/10* (2016.08); *A23L 33/105* (2016.08); *A23L 33/115* (2016.08); *A23L 33/12* (2016.08); *A23L 33/125* (2016.08); *A61K 31/047* (2013.01); *A61K 31/122* (2013.01); *A61K 31/336* (2013.01); *A61K 35/60* (2013.01); *A61K 36/185* (2013.01); *A61K 36/55* (2013.01); *A61K 47/02* (2013.01); *A61K 47/36* (2013.01); *A61K 47/42* (2013.01); *A61K 47/44* (2013.01); *A23V 2002/00* (2013.01)

(58) Field of Classification Search
CPC ..................................................... A61K 36/00
See application file for complete search history.

(56) References Cited

U.S. PATENT DOCUMENTS

| | | | |
|---|---|---|---|
| 2,800,457 A | 7/1957 | Green et al. | |
| 3,787,216 A * | 1/1974 | Wingerd ................... A23L 9/22 | 426/570 |
| 2005/0051483 A1 | 3/2005 | Majeed et al. | |
| 2008/0171032 A1 | 7/2008 | Kelly | |

FOREIGN PATENT DOCUMENTS

| | | |
|---|---|---|
| JP | H05-292899 A | 11/1993 |
| WO | 2013/161346 A1 | 10/2013 |
| WO | WO-2013161346 A1 * | 10/2013 |
| WO | 2016/020217 A1 | 2/2016 |

OTHER PUBLICATIONS

Feb. 27, 2019 Extended European Search Report issued in European Patent Application No. 18198476.6.

* cited by examiner

*Primary Examiner* — Qiuwen Mi
(74) *Attorney, Agent, or Firm* — Oliff PLC (57) ABSTRACT

A production method of an edible sustained-release functional material that has a high effect of preventing oozing of oil at the time of production, and that can inexpensively perform production, even by using fat and oil other than fish oil and continuously performing pulverization at ordinary temperature; and the edible sustained-release functional material. An edible sustained-release functional material is produced by: preparing an emulsified raw material by emulsifying fat and oil containing a hydrophobic functional ingredient; stirring and mixing the emulsified raw material, gelatin, transglutaminase, and dextrin having a DE value of 8 to 21; then forming a gel by leaving the mixture to rest; and after freeze-drying the gel, performing pulverization for powderization. An emulsifier or ammonium salt may be further added at the time of stirring and mixing.

16 Claims, 1 Drawing Sheet

PRODUCTION METHOD OF EDIBLE SUSTAINED-RELEASE FUNCTIONAL MATERIAL AND EDIBLE SUSTAINED-RELEASE FUNCTIONAL MATERIAL

FIELD OF THE INVENTION

The present invention relates to a production method of an edible sustained-release functional material, and to the edible sustained-release functional material.

DESCRIPTION OF RELATED ART

Conventionally, a powdered sustained-release functional material that contains fat and oil containing a hydrophobic functional ingredient such as DHA or EPA, gelatin, transglutaminase, and ammonium salt has been developed by the inventors of the present invention as an edible sustained-release functional material having a long retention time in the digestive tract that allows sustained release of functional ingredients contained therein (for example, see Patent Literature 1). This sustained-release functional material is produced by: forming a crosslinked gel by stirring and mixing a raw material containing fat and oil, gelatin, transglutaminase, and ammonium salt and leaving these to rest; and after lyophilizing this crosslinked gel, performing pulverization for powderization.

Since this production method of the sustained-release functional material performs preparation by pulverizing a substance in which oil droplets are dispersed in a crosslinked gel unlike a so-called coacervation method that forms a thin layer of gelatin on a surface of an oil droplet to form microcapsules one by one (for example, see Patent Literature 2 or 3), it is particularly remarkable in that a crosslinked gelatin layer for protecting fat and oil can be made thick.

CITATION LIST

Patent Literature 1: International Publication WO No. 2013/161346
Patent Literature 2: U.S. Pat. No. 2,800,457
Patent Literature 3: Japanese Unexamined Patent Application Publication No. 5-292899

SUMMARY OF THE INVENTION

The sustained-release functional material of Patent Literature 1 can effectively prevent oozing of oil at the time of pulverization after lyophilization when performing production by using fish oil and palm oil as fat and oil, and further using an emulsifier in combination. However, there was a problem that oozing of oil is difficult to be prevented when using fat and oil other than fish oil. In addition, there was also a problem that pulverization heat by frictional heat may be generated and oozing of oil may occur when a pulverizer is used for continuous pulverization at ordinary temperature at the time of pulverization after lyophilization. In order to prevent this oozing of oil, a freeze-pulverizing method in which freezing is performed at the time of pulverization can be utilized. However, there was also a problem that large cold heat energy is required, and thus a cost required for pulverization is increased.

The present invention is made by focusing on such problems, and an object thereof is to provide: a production method of an edible sustained-release functional material that has a high effect of preventing oozing of oil at the time of production, and that can inexpensively perform production, even by using fat and oil other than fish oil and continuously performing pulverization at ordinary temperature; and an edible sustained-release functional material.

Solution to Problem

In order to achieve the above-described objective, the production method of an edible sustained-release functional material defined by the present invention is characterized by: preparing an emulsified raw material by emulsifying fat and oil containing a hydrophobic functional ingredient; stirring and mixing the emulsified raw material, gelatin, transglutaminase, and dextrin having a DE value of 8 to 21; then leaving these to rest to form a gel; and after freeze-drying the gel, performing pulverization for powderization.

In addition, the edible sustained-release functional material defined by the present invention is characterized by being produced by the production method of an edible sustained-release functional material defined by the present invention.

Since the production method of an edible sustained-release functional material defined by the present invention contains dextrin, an effect of preventing oozing of oil when performing pulverization at the time of production is high even by using fat and oil other than fish oil as the fat and oil. In addition, since dextrin is contained, the effect of preventing oozing of oil is also high when continuously performing pulverization at ordinary temperature by using a commercially available pulverizer or the like at the time of production. Thereby, production can be inexpensively performed as compared to a case in which a freeze-pulverizing method is used at the time of pulverization.

In addition, by using dextrin having a DE value of 8 to 21, occurrence of foaming or shrinkage at the time of freeze-drying can be effectively prevented. Furthermore, a substance in which a gel is freeze-dried can be effectively made brittle. Thus, compression loading at the time of pulverization can be reduced, and, in particular, elution of oil due to frictional heat can be effectively prevented.

Since the edible sustained-release functional material defined by the present invention is produced by the production method of an edible sustained-release functional material defined by the present invention, each particle of produced powders has a structure in which fat and oil are surrounded by a membrane. Thereby, since digestion starts from the outer membrane in the digestive tract, a sustained-release function can be imparted to the hydrophobic functional ingredient contained in the fat and oil. In addition, since a gel is formed without causing coacervation due to leaving to rest after stirring and mixing, the membrane surrounding the fat and oil can be made thicker than that of a microcapsule produced by a conventional coacervation method, and a more advanced sustained-release ability can be obtained.

According to the production method of an edible sustained-release functional material defined by the present invention, an emulsifier may be further added at the time of stirring and mixing. The emulsifier includes, for example, sucrose fatty acid ester, polyglycerol fatty acid ester, polysorbate, polyglycerol polyricinoleate, diacylglycerol, monoacylglycerol, waxes, sterol esters, and the like. The emulsifier preferably has an HLB of 1 to 16.

According to the production method of an edible sustained-release functional material defined by the present invention, ammonium salt may be further added at the time of stirring and mixing. In this case, the time until gelling can be adjusted. The ammonium salt includes, for example, salts of ammonium, tetramethylammonium, and the like such as ammonium chloride and ammonium dihydrogen phosphate.

In the production method of an edible sustained-release functional material defined by the present invention, the above-described fat and oil preferably contain fish oil containing the above-described hydrophobic functional ingredient or hydrogenated oil in which the above-described hydrophobic functional ingredient that is oil-soluble is dissolved. The above-described hydrophobic functional ingredient includes, for example, DHA, EPA, astaxanthin, diterpene alcohol, linseed oil, fucoxanthin, and the like. The hydrophobic functional ingredient may be one having high hydrophobicity such as carotenes or one having low hydrophobicity such as xanthophylls. The fat and oil may contain two or more types of hydrophobic functional ingredients.

Advantageous Effects of Invention

The present invention can provide: a production method of an edible sustained-release functional material that has a high effect of preventing oozing of oil at the time of production, and that can inexpensively perform production, even by using fat and oil other than fish oil and continuously performing pulverization at ordinary temperature; and the edible sustained-release functional material itself.

DESCRIPTION OF EMBODIMENTS

Hereinafter, an embodiment of the present invention will be described based on various studies and examples. An edible sustained-release functional material according to the embodiment of the present invention is powdered, and it contains fat and oil containing a hydrophobic functional ingredient, gelatin, transglutaminase, and dextrin. In addition, an emulsifier or ammonium salt may also be contained. The hydrophobic functional ingredient includes, for example, DHA, EPA, astaxanthin, diterpene alcohol, linseed oil, fucoxanthin, and the like. The fat and oil may contain only one type thereof, or two or more types thereof.

The edible sustained-release functional material according to the embodiment of the present invention can be produced by the production method of an edible sustained-release functional material according to the embodiment of the present invention. More specifically, in the production method of an edible sustained-release functional material according to the embodiment of the present invention, firstly, an emulsified raw material is prepared by emulsifying fat and oil containing a hydrophobic functional ingredient by the self-emulsification ability thereof or by using an emulsifier or the like. Next, the emulsified raw material, gelatin, transglutaminase, and dextrin are stirred and mixed, and then these are left to rest to form a gel. Furthermore, after the gel is freeze-dried, pulverization is performed for powderization. Thereby, the edible sustained-release functional material according to the embodiment of the present invention can be produced.

In the edible sustained-release functional material according to the embodiment of the present invention produced in this manner, each particle of the powders has a structure in which fat and oil are surrounded by a membrane. Thereby, since digestion starts from the outer membrane in the digestive tract, a sustained-release function can be imparted to the hydrophobic functional ingredient contained in the fat and oil. In addition, since the membrane surrounding the fat and oil can be made thicker than that of a microcapsule produced by a conventional coacervation method, a more advanced sustained-release ability can be obtained.

Furthermore, since the edible sustained-release functional material according to the embodiment of the present invention contains dextrin, an effect of preventing oozing of oil when performing pulverization at the time of production is high even by using fat and oil other than fish oil as the fat and oil. In addition, since dextrin is contained, the effect of preventing oozing of oil is also high when continuously performing pulverization at ordinary temperature by using a commercially available pulverizer or the like at the time of production. Thereby, production can be inexpensively performed as compared to a case in which a freeze-pulverizing method is used at the time of pulverization.

Hereinafter, studies for examining dextrin, fat and oil, and an emulsifier, a powderization study, an oxidation stability study, and the like were conducted. Furthermore, as examples, an edible sustained-release functional material according to the embodiment of the present invention was produced by using various hydrophobic functional ingredients and fat and oil.

Production Method of Study Sample

In each study, a study sample was produced by the following method. More specifically, firstly, an emulsified liquid was prepared by adding purified fish oil as fat and oil to a solution in which an emulsifier and the like are dissolved, and then after heating to 85° C., processing the solution with a high-pressure homogenizer ("ECONIZER LABO-01" manufactured by Sanmaru Machinery Co., Ltd.) at a uniform pressure of 50 MPa and a number of revolutions of 60 rpm. At this time, the diameter of the emulsified particle was measured with a laser diffraction scattering type particle size distribution meter ("SALD-300V" manufactured by Shimadzu Corporation) in advance, and the average diameter of the emulsified particle was confirmed to be less than 1 μm.

After adjusting the temperature of the prepared emulsified liquid to 65° C., gelatin, transglutaminase, dextrin, and ammonium salt as necessary, were added to be processed with a homomixer ("TK HOMO JETTOR" manufactured by Tokushu Kika Kogyo Co., Ltd.) for 5 minutes, and these components were completely dissolved. Then after filling a prescribed container and causing gelling at 4° C., an enzyme reaction was caused overnight. The crosslinked gel mass was pulverized with a food cutter, and after lyophilization (freeze-drying), continuous pulverization at ordinary temperature was performed using an electric mill ("Wonder Crusher WC-3" manufactured by OSAKA CHEMICAL Co., Ltd.). In this manner, a study sample of the powdered sustained-release functional material was produced.

Study 1: Examination on Dextrin and the Like

Various kinds of dextrin having different DE values, powdered starch syrup, and glucose were formulated, and examinations were made on the degree of influence on brittleness due to lyophilization. In this regard, the DE value (Dextrose Equivalent) is a value in which the amount of reducing sugar that is regarded as the amount of glucose is expressed as percentages with respect to the solid content, wherein a DE value closer to 0 indicates the property of starch, and a DE value closer to 100 indicates a property similar to glucose. The study was conducted with formulations of Tests 1 to 7 shown in Table 1.

| FORMULA TESTED | | | | | | | |
|---|---|---|---|---|---|---|---|
| | TEST ① | TEST ② | TEST ③ | TEST ④ | TEST ⑤ | TEST ⑥ | TEST ⑦ |
| PURIFIED FISH OIL | 20.00% | 20.00% | 20.00% | 20.00% | 20.00% | 20.00% | 20.00% |
| PALM OIL (MELTING POINT 50° C.) | 2.00% | 2.00% | 2.00% | 2.00% | 2.00% | 2.00% | 2.00% |
| GELATIN | 15.00% | 15.00% | 15.00% | 15.00% | 15.00% | 15.00% | 15.00% |
| AMMONIUM PHOSPHATE | 0.04% | 0.04% | 0.04% | 0.04% | 0.04% | 0.04% | 0.04% |
| SUCROSE FATTY ACID ESTER (HLB 1) | 0.32% | 0.32% | 0.32% | 0.32% | 0.32% | 0.32% | 0.32% |
| SUCROSE FATTY ACID ESTER (HLB 16) | 0.64% | 0.64% | 0.64% | 0.64% | 0.64% | 0.64% | 0.64% |
| TRANSGLUTAMINASE | 80 ppm | 80 ppm | 80 ppm | 80 ppm | 80 ppm | 80 ppm | 80 ppm |
| DEXTRIN (DE8~10) | 0.00% | 4.00% | — | — | — | — | — |
| DEXTRIN (DE12~15) | — | — | 4.00% | — | — | — | — |
| DEXTRIN (DE17~21) | — | — | — | 4.00% | — | — | — |
| DEXTRIN (DE24~26) | — | — | — | — | 4.00% | — | — |
| POWDERED STARCH SYRUP (DE28~32) | — | — | — | — | — | 4.00% | — |
| GLUCOSE (DE100) | — | — | — | — | — | — | 4.00% |
| CITY WATER | REMAINING AMOUNT | | | | | | |
| TOTAL | 100.00% | | | | | | |

In the study, firstly, samples of a crosslinked gel mass before lyophilization were produced with each of the formulations. Each sample was cut into a number of cuboids of 1 cm×1 cm×1 cm, and after preliminary freezing for 8 hours in a freezer at −80° C., lyophilization (degree of vacuum 10 pa) was conducted for 24 hours. Each lyophilized sample was observed, and the collapse rate was determined by counting those in which foaming or shrinkage was recognized as collapse, and calculating the ratio from the total number thereof. The formula for determining the collapse rate is shown in Formula (1).

$$\text{collapse rate (\%)} = \frac{\text{those in which collapse has occurred (units)}}{\text{total number (units)}} \times 100 \quad (1)$$

In addition, as an index of brittleness, the rupture stress and the rupture distortion factor of lyophilized cuboid samples were measured by using a creep meter ("Creep Meter RE-3305" manufactured by Yamaden Co., Ltd.). At this time, a detector was set to 20 kg, and a plunger for shearing (knife type) was used, while a load was applied at 1 mm/sec. The determined collapse rate, rupture stress, and rupture distortion factor of each of the samples are shown in Table 2.

tion had an influence, and thus a hard layer of gelatin was formed due to the occurrence of partial shrinkage. In contrast, in Tests 2 to 6 where dextrin and the like were formulated, the rupture stress and the rupture distortion factor tended to be smaller compared to those in Test 1, and it is understood that brittleness was caused. It should be noted that, in Test 7, since elution of oil occurred from immediately after the completion of lyophilization, the rupture stress and the rupture distortion factor could not be measured.

In addition, as shown in Table 2, although the collapse rate was reduced by formulating dextrin and the like, at the time of a large DE value of 24 or higher (Tests 5 to 7), a high collapse rate of 70% or higher was still confirmed. In contrast, when the DE value was in the range of 8 to 21 (Tests 2 to 4), the collapse rate became 10% or lower, and collapses were confirmed to be substantially prevented.

It should be noted that, in Test 7, disintegration/melting occurred after shrinkage as compared to Test 1, and lyophilization was not conducted well. In general, it has been known that collapse is likely to occur if preliminary freezing was conducted at a lower temperature than the collapse temperature, and collapse temperatures are lower in low molecular sugars (for example, the collapse temperature of glucose is −40° C.). It is considered that, in a case where the DE value is high and a low molecular sugar is contained as in Test 7, a layer that is difficult to be frozen was

| FORMULA TESTED | | | | | | | |
|---|---|---|---|---|---|---|---|
| | TEST ① | TEST ② | TEST ③ | TEST ④ | TEST ⑤ | TEST ⑥ | TEST ⑦ |
| COLLAPSE RATE | 100.00% | 9.50% | 3.90% | 0.00% | 85.40% | 77.20% | 100.00% |
| RUPTURE STRESS | $3.4 \times 10^7$ N/m² | $2.4 \times 10^7$ N/m² | $2.3 \times 10^7$ N/m² | $2.0 \times 10^7$ N/m² | $4.4 \times 10^6$ N/m² | $2.5 \times 10^6$ N/m² | — |
| RUPTURE DISTORTION | 24.90% | 14.70% | 14.30% | 13.60% | 16.20% | 15.70% | — |

As shown in Table 2, in Test 1 where dextrin, powdered starch syrup, and glucose were not formulated, the rupture stress was larger compared to that of other study sections, and the rupture distortion factor was also higher. Thus, the sample was regarded as being hard and difficult to be ruptured. It is considered that this was because, since the collapse rate was 100%, collapses at the time of lyophilizagenerated at the stage of preliminary freezing, and melting occurred due to partial concentration during lyophilization.

Study 2: Powderization Study

Each cuboid sample produced with the formulations of Tests 1 to 7 shown in Table 1 was continuously pulverized with an electric mill, and oozing of fish oil at the time of pulverization was confirmed. The results are shown in Table 3. The evaluation criteria for Table 3 are as follows.
Evaluation Criteria
○: no oozing of fish oil; Δ: slight oozing of fish oil; x: oozing of fish oil

| | Formula tested | | | | | | |
|---|---|---|---|---|---|---|---|
| | Test ① | Test ② | Test ③ | Test ④ | Test ⑤ | Test ⑥ | Test ⑦ |
| Oozing of fish oil | Δ | ○ | ○ | ○ | Δ | Δ | X |

As shown in Table 3, in Tests 2 to 4 where dextrin having a DE value of 8 to 21 is formulated, oozing of fish oil was not confirmed after pulverization. In contrast, slight oozing of fish oil was confirmed in Test 1 where dextrin and the like were not formulated, and in Tests 5 to 6 where the DE value was 24 or higher. In Test 7, since oozing of fish oil occurred from before pulverization, pulverization could not be performed.

Figure 1:
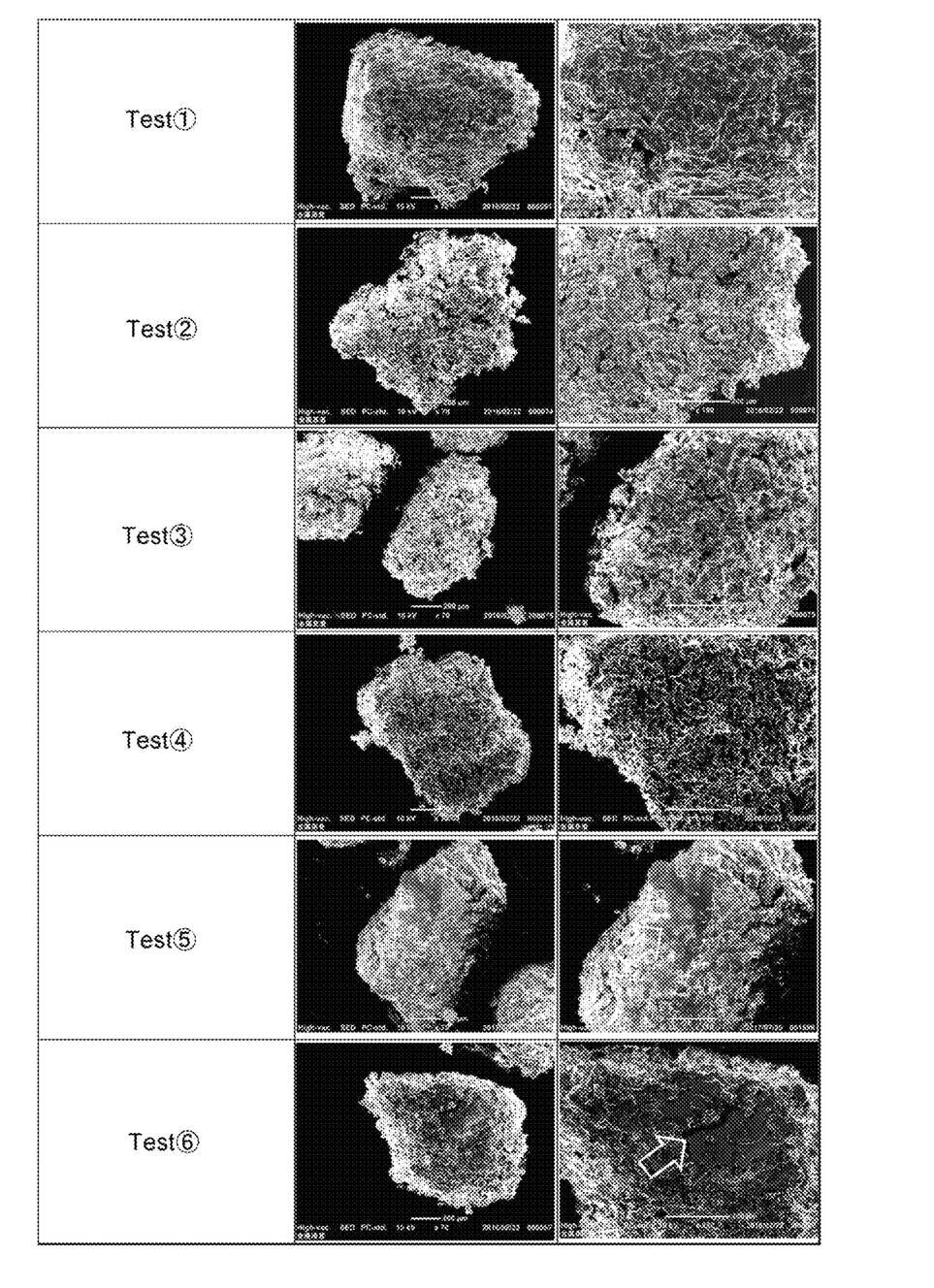
FIG. 1 is an electron microscope picture showing particles of each of the powdered samples produced by formulating dextrin having different DE values using the production method of an edible sustained-release functional material according to an embodiment of the present invention.

Next, pulverized powders were observed using an electron microscope, and the results are shown in Table 1. It should be noted that, by observing the cross section of fractures after pulverization, deformation and brittleness until the occurrence of a fracture can be confirmed. The fracture morphology includes ductile fracture, in which large plastic deformation is caused before the occurrence of fracture, and brittle fracture, in which plastic deformation is hardly caused before the occurrence of fracture.

As shown in FIG. 1, plastic deformation in Test 1 is likely to be caused due to the influence of a load applied at the time of pulverization, and the appearance of a ductile fracture surface was confirmed. In Tests 2 to 4, brittleness was caused by formulating dextrin, and the occurrence of brittle fractures that do not involve deformation was confirmed. Although pulverization could be performed in Tests 5 and 6, exposure of an oil layer (the arrow in the FIGURE) on a smooth surface was confirmed due to the influence of the collapse. Thus, also from the result of FIG. 1, it was confirmed that the collapse rate was decreased by formulating dextrin, and brittleness was caused.

From the results of Studies 1 and 2, it was understood that by formulating dextrin having a DE value of 8 to 21, particularly preferably a DE value of 12 to 21, occurrence of foaming or shrinkage at the time of lyophilization can be prevented, while those being lyophilized can be made brittle, and thus a compression load at the time of pulverization can be reduced, and elution of oil due to frictional heat can be effectively prevented. Thus, continuous pulverization at ordinary temperature can be performed by using a commercially available pulverizer or the like without the elution of oil, and a sustained-release functional material can be inexpensively produced without the use of a freeze-pulverizing method.

Study 3: Examination on Formulation Amount of Dextrin

Since the load at the time of pulverization may be reduced depending on the formulation amount of dextrin, an examination was conducted on appropriate formulation amounts. The study was conducted with the formulations of Tests 1 to 6 shown in Table 4. Dextrin having a DE value of 17 to 21 was used. In the study, the collapse rate, the rupture stress, and the rupture distortion factor were determined by the same method as in Study 1. The results are shown in Table 5.

| | Formula tested | | | | | |
|---|---|---|---|---|---|---|
| | Test ① | Test ② | Test ③ | Test ④ | Test ⑤ | Test ⑥ |
| Purified fish oil | 20.00% | 20.00% | 20.00% | 20.00% | 20.00% | 20.00% |
| Palm oil (melting point 50° C.) | 2.00% | 2.00% | 2.00% | 2.00% | 2.00% | 2.00% |
| Gelatin | 15.00% | 15.00% | 15.00% | 15.00% | 15.00% | 15.00% |
| Ammonium phosphate | 0.04% | 0.04% | 0.04% | 0.04% | 0.04% | 0.04% |
| Sucrose fatty acid ester (HLB 1) | 0.32% | 0.32% | 0.32% | 0.32% | 0.32% | 0.32% |
| Sucrose fatty acid ester (HLB 16) | 0.64% | 0.64% | 0.64% | 0.64% | 0.64% | 0.64% |
| Transglutaminase | 80 ppm | 80 ppm | 80 ppm | 80 ppm | 80 ppm | 80 ppm |
| Dextrin (DE17~21) | 0.00% | 1.00% | 2.00% | 3.00% | 4.00% | 5.00% |
| City water | Remaining amount | | | | | |
| Total | 100.00% | | | | | |

| | Formula tested | | | | | |
|---|---|---|---|---|---|---|
| | Test ① | Test ② | Test ③ | Test ④ | Test ⑤ | Test ⑥ |
| Collapse rate | 100.00% | 4.00% | 0.00% | 0.00% | 0.00% | 0.00% |
| Rupture stress | $3.4 \times 10^7$ N/m$^2$ | $3.1 \times 10^7$ N/m$^2$ | $2.6 \times 10^7$ N/m$^2$ | $2.3 \times 10^7$ N/m$^2$ | $2.0 \times 10^7$ N/m$^2$ | $1.9 \times 10^7$ N/m$^2$ |
| Rupture distortion | 24.90% | 21.20% | 21.10% | 16.80% | 13.60% | 13.50% |

As shown in Table 5, it was confirmed that the collapse rate at the time of lyophilization could be reduced by formulating dextrin by 1% or higher. In addition, the larger the formulation amount of dextrin, the rupture strength and the rupture distortion factor can be decreased, and it was confirmed that brittleness is likely to be caused depending on the formulation amount of dextrin.

Study 4: Examination on Presence or Absence of Palm Fat and Oil

Patent Literature 1 indicates that fat and oil (hydrogenated fat and oil) having a high melting point such as palm oil need to be used in combination in order to prevent fish oil from oozing when being powdered. It is considered that this is because, in addition to generation of pulverization heat by frictional heat and the like at the time of pulverization due to hardness of the sample after lyophilization, partial compression occurs within the sample due to the influence of ductile fracture, and thus elution of oil would occur in oil having a low melting point such as purified fish oil unless hydrogenated fat and oil are formulated.

Since brittleness can be achieved by formulating appropriate dextrin, it is considered that frictional heat at the time of pulverization may be reduced, and pulverization may be performed without oozing of oil even if palm fat and oil are not formulated. Thus, an examination was conducted on the formulation amount of palm fat and oil. The study was conducted with the formulations of Tests 1 to 6 shown in Table 6. Dextrin having a DE value of 17 to 21 was used.

|  | Formula tested | | | | | |
|---|---|---|---|---|---|---|
|  | Test ① | Test ② | Test ③ | Test ④ | Test ⑤ | Test ⑥ |
| Purified fish oil | 20.00% | 20.00% | 20.00% | 20.00% | 20.00% | 20.00% |
| Palm oil (melting point 50° C.) | 2.50% | 2.00% | 1.50% | 1.25% | 0.63% | 0.00% |
| Gelatin | 15.00% | 15.00% | 15.00% | 15.00% | 15.00% | 15.00% |
| Ammonium phosphate | 0.04% | 0.04% | 0.04% | 0.04% | 0.04% | 0.04% |
| Sucrose fatty acid ester (HLB 1) | 0.32% | 0.32% | 0.32% | 0.32% | 0.32% | 0.32% |
| Sucrose fatty acid ester (HLB 16) | 0.64% | 0.64% | 0.64% | 0.64% | 0.64% | 0.64% |
| Transglutaminase | 80 ppm | 80 ppm | 80 ppm | 80 ppm | 80 ppm | 80 ppm |
| Dextrin (DE17~21) | 4.00% | 4.00% | 4.00% | 4.00% | 4.00% | 4.00% |
| City water | Remaining amount | | | | | |
| Total | 100.00% | | | | | |

In the study, the collapse rate, the rupture stress, and the rupture distortion factor of each sample in Tests 1 to 6 were determined by the same method as in Study 1. The results are shown in Table 7. In addition, oozing of fish oil at the time of pulverization was also confirmed. The results are shown in Table 8. The evaluation criteria for Table 8 are as follows.

Evaluation Criteria
○: no oozing of fish oil; Δ: slight oozing of fish oil; x: oozing of fish oil

|  | Formula tested | | | | | |
|---|---|---|---|---|---|---|
|  | Test ① | Test ② | Test ③ | Test ④ | Test ⑤ | Test ⑥ |
| Oozing of fish oil | ○ | ○ | ○ | ○ | ○ | ○ |

As shown in Table 7, collapse did not occur in any of Tests 1 to 6, and no significant difference was observed in the rupture stress and the rupture distortion factor. In addition, as shown in Table 8, oozing of oil was not observed in any of Tests 1 to 6, and it was confirmed that oozing of oil could be prevented even if palm fat and oil were not formulated into fish oil. It is considered that this supports the fact that a reduction of a pulverization load due to brittleness is enabled by formulating dextrin.

Study 5: Examination on Emulsifier

Patent Literature 1 indicates that, in order to emulsify a mixture of fish oil and fat and oil having a high melting point, the selection of a suitable emulsifier is important. From Study 4, it was confirmed that pulverization at ordinary temperature is enabled regardless of the presence or absence of palm fat and oil. Thus, it is considered that a limitation to a specific emulsifier is not necessary if emulsification of purified fish oil and formulated water is stable (creaming or demulsification has not occurred). Therefore, an examination was conducted on the emulsifier.

The study was conducted with the formulations of Tests 1 to 18 shown in Table 9 and Tests 19 to 34 shown in Table 10. Table 9 shows those in which a single emulsifier was formulated, and Table 10 shows those in which emulsifiers having different HLBs were combined. In addition, for each different formulation condition of the emulsifiers, a study was conducted on that in which palm fat and oil are formulated or not formulated. Dextrin having a DE value of 17 to 21 was used. A sucrose fatty acid ester having an HLB of 1 to 16 was used as the emulsifier.

|  | Formula tested | | | | | |
|---|---|---|---|---|---|---|
|  | Test ① | Test ② | Test ③ | Test ④ | Test ⑤ | Test ⑥ |
| Collapse rate | 0.00% | 0.00% | 0.00% | 0.00% | 0.00% | 0.00% |
| Rupture stress | $1.9 \times 10^7$ N/m$^2$ | $2.0 \times 10^7$ N/m$^2$ | $2.1 \times 10^7$ N/m$^2$ | $2.0 \times 10^7$ N/m$^2$ | $1.8 \times 10^7$ N/m$^2$ | $1.9 \times 10^7$ N/m$^2$ |
| Rupture distortion | 14.00% | 13.60% | 13.90% | 12.90% | 13.60% | 14.00% |

|  | HLB 1 | | HLB 2 | | HLB 3 | | HLB 5 | | HLB 7 | |
|---|---|---|---|---|---|---|---|---|---|---|
|  | \[colspan=10\] Formula tested | | | | | | | | | |
|  | Test ① | Test ② | Test ③ | Test ④ | Test ⑤ | Test ⑥ | Test ⑦ | Test ⑧ | Test ⑨ | Test ⑩ |
| Purified fish oil | 20.00% | 20.00% | 20.00% | 20.00% | 20.00% | 20.00% | 20.00% | 20.00% | 20.00% | 20.00% |
| Palm oil (melting point 50° C.) | 2.00% | 0.00% | 2.00% | 0.00% | 2.00% | 0.00% | 2.00% | 0.00% | 2.00% | 0.00% |
| Gelatin | 15.00% | 15.00% | 15.00% | 15.00% | 15.00% | 15.00% | 15.00% | 15.00% | 15.00% | 15.00% |
| Ammonium phosphate | 0.04% | 0.04% | 0.04% | 0.04% | 0.04% | 0.04% | 0.04% | 0.04% | 0.04% | 0.04% |
| Sucrose fatty acid ester (HLB 1) | 0.96% | 0.96% | — | — | — | — | — | — | — | — |
| Sucrose fatty acid ester (HLB 2) | — | — | 0.96% | 0.96% | — | — | — | — | — | — |
| Sucrose fatty acid ester (HLB 3) | — | — | — | — | 0.96% | 0.96% | — | — | — | — |
| Sucrose fatty acid ester (HLB 5) | — | — | — | — | — | — | 0.96% | 0.96% | — | — |
| Sucrose fatty acid ester (HLB 7) | — | — | — | — | — | — | — | — | 0.96% | 0.96% |
| Sucrose fatty acid ester (HLB 9) | — | — | — | — | — | — | — | — | — | — |
| Sucrose fatty acid ester (HLB 11) | — | — | — | — | — | — | — | — | — | — |
| Sucrose fatty acid ester (HLB 15) | — | — | — | — | — | — | — | — | — | — |
| Sucrose fstty acid ester (HLB 16) | — | — | — | — | — | — | — | — | — | — |
| Transglutaminase | 80 ppm | 80 ppm | 80 ppm | 80 ppm | 80 ppm | 80 ppm | 80 ppm | 80 ppm | 80 ppm | 80 ppm |
| Dextrin (DE17~21) | 4.00% | 4.00% | 4.00% | 4.00% | 4.00% | 4.00% | 4.00% | 4.00% | 4.00% | 4.00% |
| Antioxidant | 0.35% | 0.35% | 0.35% | 0.35% | 0.35% | 0.35% | 0.35% | 0.35% | 0.35% | 0.35% |
| Trisodium phosphate | 0.15% | 0.15% | 0.15% | 0.15% | 0.15% | 0.15% | 0.15% | 0.15% | 0.15% | 0.15% |
| City water | \[colspan=10\] Remaining water | | | | | | | | | |
| Total | \[colspan=10\] 100.00% | | | | | | | | | |

|  | HLB 9 | | HLB 11 | | HLB 15 | | HLB 16 | |
|---|---|---|---|---|---|---|---|---|
|  | \[colspan=8\] Formula tested | | | | | | | |
|  | Test ⑪ | Test ⑫ | Test ⑬ | Test ⑭ | Test ⑮ | Test ⑯ | Test ⑰ | Test ⑱ |
| Purified fish oil | 20.00% | 20.00% | 20.00% | 20.00% | 20.00% | 20.00% | 20.00% | 20.00% |
| Palm oil (melting point 50° C.) | 2.00% | 0.00% | 2.00% | 0.00% | 2.00% | 0.00% | 2.00% | 0.00% |
| Gelatin | 15.00% | 15.00% | 15.00% | 15.00% | 15.00% | 15.00% | 15.00% | 15.00% |
| Ammonium phosphate | 0.04% | 0.04% | 0.04% | 0.04% | 0.04% | 0.04% | 0.04% | 0.04% |
| Sucrose fatty acid ester (HLB 1) | — | — | — | — | — | — | — | — |
| Sucrose fatty acid ester (HLB 2) | — | — | — | — | — | — | — | — |
| Sucrose fatty acid ester (HLB 3) | — | — | — | — | — | — | — | — |
| Sucrose fatty acid ester (HLB 5) | — | — | — | — | — | — | — | — |
| Sucrose fatty acid ester (HLB 7) | — | — | — | — | — | — | — | — |
| Sucrose fatty acid ester (HLB 9) | 0.96% | 0.96% | — | — | — | — | — | — |
| Sucrose fatty acid ester (HLB 11) | — | — | 0.96% | 0.96% | — | — | — | — |
| Sucrose fatty acid ester (HLB 15) | — | — | — | — | 0.96% | 0.96% | — | — |
| Sucrose fatty acid ester (HLB 16) | — | — | — | — | — | — | 0.96% | 0.96% |
| Transglutaminase | 80 ppm | 80 ppm | 80 ppm | 80 ppm | 80 ppm | 80 ppm | 80 ppm | 80 ppm |
| Dextrin (DE17~21) | 4.00% | 4.00% | 4.00% | 4.00% | 4.00% | 4.00% | 4.00% | 4.00% |
| Antioxidant | 0.35% | 0.35% | 0.35% | 0.35% | 0.35% | 0.35% | 0.35% | 0.35% |
| Trisodium phosphate | 0.15% | 0.15% | 0.15% | 0.15% | 0.15% | 0.15% | 0.15% | 0.15% |
| City water | \[colspan=8\] Remaining water | | | | | | | |
| Total | \[colspan=8\] 100.00% | | | | | | | |

|  | HLB 1/HLB 16 | | HLB 2/HLB 15 | | HLB 3/HLB 11 | | HLB 5/HLB 9 | |
|---|---|---|---|---|---|---|---|---|
|  | \[colspan=8\] Formula tested | | | | | | | |
|  | Test ⑲ | Test ⑳ | Test ㉑ | Test ㉒ | Test ㉓ | Test ㉔ | Test ㉕ | Test ㉖ |
| Purified fish oil | 20.00% | 20.00% | 20.00% | 20.00% | 20.00% | 20.00% | 20.00% | 20.00% |
| Palm oil (melting point 50° C.) | 2.00% | 0.00% | 2.00% | 0.00% | 2.00% | 0.00% | 2.00% | 0.00% |
| Gelatin | 15.00% | 15.00% | 15.00% | 15.00% | 15.00% | 15.00% | 15.00% | 15.00% |
| Ammonium phosphate | 0.04% | 0.04% | 0.04% | 0.04% | 0.04% | 0.04% | 0.04% | 0.04% |
| Sucrose fatty acid ester (HLB 1) | 0.32% | 0.32% | — | — | — | — | — | — |
| Sucrose fatty acid ester (HLB 2) | — | — | 0.32% | 0.32% | — | — | — | — |
| Sucrose fatty acid ester (HLB 3) | — | — | — | — | 0.32% | 0.32% | — | — |
| Sucrose fatty acid ester (HLB 5) | — | — | — | — | — | — | 0.32% | 0.32% |
| Sucrose fatty acid ester (HLB 7) | — | — | — | — | — | — | — | — |
| Sucrose fatty acid ester (HLB 9) | — | — | — | — | — | — | 0.64% | 0.64% |
| Sucrose fatty acid ester (HLB 11) | — | — | — | — | 0.64% | 0.64% | — | — |
| Sucrose fatty acid ester (HLB 15) | — | — | 0.64% | 0.64% | — | — | — | — |
| Sucrose fatty acid ester (HLB 16) | 0.64% | 0.64% | — | — | — | — | — | — |
| Transglutaminase | 80 ppm | 80 ppm | 80 ppm | 80 ppm | 80 ppm | 80 ppm | 80 ppm | 80 ppm |
| Dextrin (DE17~21) | 4.00% | 4.00% | 4.00% | 4.00% | 4.00% | 4.00% | 4.00% | 4.00% |

|  | | | | | | | | |
|---|---|---|---|---|---|---|---|---|
| Antioxidant | 0.35% | 0.35% | 0.35% | 0.35% | 0.35% | 0.35% | 0.35% | 0.35% |
| Trisodium phosphate | 0.15% | 0.15% | 0.15% | 0.15% | 0.15% | 0.15% | 0.15% | 0.15% |
| City water | | | | Remaining water | | | | |
| Total | | | | 100.00% | | | | |

| | HLB 16/HLB 1 | | HLB 15/HLB 2 | | HLB 11/HLB 3 | | HLB 9/HLB 5 | |
|---|---|---|---|---|---|---|---|---|
| | Formula tested | | | | | | | |
| | Test 27 | Test 28 | Test 29 | Test 30 | Test 31 | Test 32 | Test 33 | Test 34 |
| Purified fish oil | 20.00% | 20.00% | 20.00% | 20.00% | 20.00% | 20.00% | 20.00% | 20.00% |
| Palm oil (melting poiet 50° C.) | 2.00% | 0.00% | 2.00% | 0.00% | 2.00% | 0.00% | 2.00% | 0.00% |
| Gelatin | 15.00% | 15.00% | 15.00% | 15.00% | 15.00% | 15.00% | 15.00% | 15.00% |
| Ammonium phosphate | 0.04% | 0.04% | 0.04% | 0.04% | 0.04% | 0.04% | 0.04% | 0.04% |
| Sucrose fatty acid ester (HLB 1) | 0.64% | 0.64% | — | — | — | — | — | — |
| Sucrose fatty acid ester (HLB 2) | — | — | 0.64% | 0.64% | — | — | — | — |
| Sucrose fatty acid ester (HLB 3) | — | — | — | — | 0.64% | 0.64% | — | — |
| Sucrose fatty acid ester (HLB 5) | — | — | — | — | — | — | 0.64% | 0.64% |
| Sucrose fatty acid ester (HLB 7) | — | — | — | — | — | — | — | — |
| Sucrose fatty acid ester (HLB 9) | — | — | — | — | — | — | 0.32% | 0.32% |
| Sucrose fatty acid ester (HLB 11) | — | — | — | — | 0.32% | 0.32% | — | — |
| Sucrose fatty acid ester (HLB 15) | — | — | 0.32% | 0.32% | — | — | — | — |
| Sucrose fatty acid ester (HLB 16) | 0.32% | 0.32% | — | — | — | — | — | — |
| Transglutaminase | 80 ppm | 80 ppm | 80 ppm | 80 ppm | 80 ppm | 80 ppm | 80 ppm | 80 ppm |
| Dextrin (DE17~21) | 4.00% | 4.00% | 4.00% | 4.00% | 4.00% | 4.00% | 4.00% | 4.00% |
| Antioxidant | 0.35% | 0.35% | 0.35% | 0.35% | 0.35% | 0.35% | 0.35% | 0.35% |
| Trisodium phosphate | 0.15% | 0.15% | 0.15% | 0.15% | 0.15% | 0.15% | 0.15% | 0.15% |
| City water | | | | Remaining water | | | | |
| Total | | | | 100.00% | | | | |

In the study, oozing of fish oil at the time of pulverization was confirmed. The results are shown in Table 1. The evaluation criteria for Table 11 are as follows.

Evaluation Criteria
○: no oozing of fish oil
Δ: slight oozing of fish oil
x: oozing of fish oil
xx: unstable emulsification (creaming/demulsification/separation)

| | Section tested | | | | | | | | | |
|---|---|---|---|---|---|---|---|---|---|---|
| | Test 1 | Test 2 | Test 3 | Test 4 | Test 5 | Test 6 | Test 7 | Test 8 | Test 9 | Test 10 |
| Oozing of fish oil | xx | xx | xx | xx | Δ | Δ | Δ | Δ | Δ | Δ |

| | Section tested | | | | | | | |
|---|---|---|---|---|---|---|---|---|
| | Test 11 | Test 12 | Test 13 | Test 14 | Test 15 | Test 16 | Test 17 | Test 18 |
| Oozing of fish oil | Δ | Δ | xx | xx | xx | xx | xx | xx |

| | Section tested | | | | | | | |
|---|---|---|---|---|---|---|---|---|
| | Test 19 | Test 20 | Test 21 | Test 22 | Test 23 | Test 24 | Test 25 | Test 26 |
| Oozing of fish oil | ○ | ○ | ○ | ○ | ○ | ○ | ○ | ○ |

| | Section tested | | | | | | | |
|---|---|---|---|---|---|---|---|---|
| | Test 27 | Test 28 | Test 29 | Test 30 | Test 31 | Test 32 | Test 33 | Test 34 |
| Oozing of fish oil | Δ | Δ | ○ | ○ | ○ | ○ | ○ | ○ |

As shown in Table 11, Tests 1 to 4 and 13 to 18 did not reach pulverization due to creaming, demulsification, or separation occurring at the emulsification step. Although pulverization at ordinary temperature was enabled in Tests 5 to 12, 27, and 28, slight oozing of oil was confirmed. In Tests 19 to 26 and 29 to 34, it was confirmed that pulverization at ordinary temperature was enabled without oozing of oil. From this result, it was confirmed that pulverization at ordinary temperature could be performed without a limitation on the selection of palm fat and oil and an emulsifier, by formulating appropriate dextrin while stabilizing the emulsification.

Japanese Unexamined Patent Application Publication No. 2011-193842, which was published by the inventors of the present invention, indicates that a time until gelling can be adjusted by formulating ammonium salt. In this Japanese Unexamined Patent Application Publication No. 2011-193842, since an enzyme reaction can be slowed by formulating ammonium salt, formulation of ammonium salt was necessary for production. However, if a given container can be filled within 5 minutes, there is no need to formulate ammonium salt. Thus, an examination was conducted on the formulation of ammonium salt. The study was conducted with the formulations of the comparative example (that in which ammonium phosphate is formulated) and the example (that in which ammonium phosphate is not formulated) shown in Table 12. Dextrin having a DE value of 17 to 21 was used.

|  | Formula tested | |
| --- | --- | --- |
|  | Comparative example | Example |
| Purified fish oil | 20.00% | 20.00% |
| Palm oil (melting point 50° C.) | 1.25% | 1.25% |
| Gelatin | 15.00% | 15.00% |
| Ammonium phosphate | 0.04% | — |
| Sucrose fatty acid ester (HLB 1) | 0.32% | 0.32% |
| Sucrose fatty acid ester (HLB 16) | 0.64% | 0.64% |
| Transglutaminase | 80 ppm | 80 ppm |
| Dextrin (DE17~21) | 4.00% | 4.00% |
| City water | Remaining amount | |
| Total | 100.00% | |

In the study, the collapse rate, the rupture stress, and the rupture distortion factor of each sample in the comparative example and the example were determined by the same method as in Study 1. In addition, oozing of fish oil at the time of pulverization was also confirmed. The results are shown in Table 13. The evaluation criteria for oozing of fish oil in Table 13 are as follows.

Evaluation Criteria

○: no oozing of fish oil, Δ: slight oozing of fish oil, x: oozing of fish oil

|  | Formula tested | |
| --- | --- | --- |
|  | Comparative example | Example |
| Collapse rate | 0.00% | 0.00% |
| Rupture stress | $2.0 \times 10^7$ N/m$^2$ | $2.0 \times 10^7$ N/m$^2$ |
| Rupture distortion | 13.60% | 13.80% |
| Oozing of fish oil | ○ | ○ |

As shown in Table 13, collapse did not occur in either of the comparative example or the example, and a significant difference was not observed in the rupture stress and the rupture distortion factor. In addition, oozing of oil was not observed in either of the comparative example and the example, and it was confirmed that oozing of oil could be prevented regardless of the formulation of ammonium salt.

Study 6: Oxidation Stability Study

Studies 1 to 3 and the like confirmed that brittleness is caused by formulating appropriate dextrin. However, since there is a concern over the instability of oxidation due to brittleness, a study of measuring peroxide value (POV) over time was conducted as the oxidation stability study. The study was conducted with the formulations of Tests 1 and 2 shown in Table 14, which are different in the presence or absence of palm oil. In addition, the same study was conducted on that in which palm oil is formulated and dextrin is not formulated, as a comparative section. Dextrin having a DE value of 17 to 21 was used. Sucrose fatty acid ester having an HLB of 1 and 16 was used as the emulsifier.

|  | Formula tested | | |
| --- | --- | --- | --- |
|  | Comparative example | Test ① | Test ② |
| Purified fish oil | 20.00% | 20.00% | 20.00% |
| Palm oil (melting point 50° C.) | 2.00% | 2.00% | 0.00% |
| Gelatin | 15.00% | 15.00% | 15.00% |
| Ammonium phosphate | 0.04% | 0.04% | 0.04% |
| Sucrose fatty acid ester (HLB 1) | 0.32% | 0.32% | 0.32% |
| Sucrose fatty acid ester (HLB 16) | 0.64% | 0.64% | 0.64% |
| Transglutaminase | 80 ppm | 80 ppm | 80 ppm |
| Dextrin (DE17~21) | 0.00% | 4.00% | 4.00% |
| Antioxidant | 0.35% | 0.35% | 0.35% |
| Trisodium phosphate | 0.15% | 0.15% | 0.15% |
| City water | Remaining water | | |
| Total | 100.00% | | |

In the study, each powdered sample produced with each of the formulations of Tests 1 and 2 and the comparative section were put in aluminum bags, and these were preserved for 30 days under the condition of a temperature of 40° C. and a humidity of 70% to be analyzed over time by potentiometric titration. The analysis used an automatic titrator (manufactured by Metrohm AG) while using a chloroform-acetic acid mixture (chloroform 2:acetic acid 3) as a solvent, and titration was performed in 0.01N sodium thiosulfate standard solution to determine the peroxide value (POV). The peroxide values (POV) before preservation and after 30 days of preservation are shown in Table 15. In addition, a general evaluation of the numerical values of the peroxide value is shown in Table 16.

| POV (meq/kg) | Comparative example | Test ① | Test ② |
| --- | --- | --- | --- |
| Day 0 | 3.00 | 2.64 | 3.00 |
| Day 30 | 13.11 | 12.47 | 13.02 |

| POV (meq/kg) | Evaluation |
| --- | --- |
| 0-10 | Almost no oxidation. |
| 10-30 | Oxidation starts to proceed. |
| 30-40 | Start feeling oxidized odor. |
| 40-50 | Better not to eat. |
| 50 or more | Serious oxidation. Risk of poisoning. |

Excluding the comparative section, collapse did not occur in the samples after lyophilization in Tests 1 and 2, and oozing of oil at the time of pulverization at ordinary temperature was also not observed. As shown in Table 15, when comparing the numerical values of the peroxide value (POV) for 30 days, a significant difference was not observed in the numerical values of the peroxide value regardless of the presence or absence of palm fat and oil in Tests 1 and 2. In addition, the degree of oxidation was confirmed to be low in all of Tests 1 and 2 and the comparative section regardless of the preservation for 30 days at a temperature of 40° C. and a humidity of 70%. From these results, a difference in the peroxide value due to the formulation of dextrin or formulation of palm fat and oil was not observed, and it was confirmed that neither of these affects the oxidation stability.

Next, a qualitative determination was made on propanal, which serves as an index of lipid oxidation of fish oil, using a headspace (HS) GC/MS method ("HS-20, QP2010-Ultra" manufactured by Shimadzu Corporation), and the peak areas were compared. In the study, firstly, 0.2 g of each powdered sample produced with each of the formulations of Tests 1 and 2, and the comparative section in Table 14 was put in a vial bottle (20 ml capacity) and tightly stopped. Then, with a vial heating temperature of 80° C. and a heating time of 30 minutes, gas in the gas phase of the vial bottle was captured/concentrated in an electronic cooling trap. The concentrated gas was separated with a column DB-WAX (manufactured by J&W; 0.32 mm×60 m) at a column temperature of 40° C. (10 min hold) and 40° C.→230° C. (rate: 10° C./min) by carrier gas (helium), and a peak was obtained with a mass spectrometer that is a detector. The measurement result was analyzed by matching with the mass spectrum in the database of NIST14. The analysis results are shown in Table 17.

| Propanal peak area | Comparative section | Test ① | Test ② |
|---|---|---|---|
| Day 0 | 0.00 | 0.00 | 0.00 |
| Day 30 | 122572.00 | 0.00 | 0.00 |

As shown in Table 17, propanal, which is an unpleasant odor, was not detected in either of Tests 1 and 2. In the comparative section, propanal was detected from the powders after a lapse of 30 days. It is considered that this is because of the influence of occurrence of slight oil oozing at the time of pulverization.

Example 1

A sustained-release functional material was produced according to the formulation of the example shown in Table 18. More specifically, firstly, purified fish oil was added to a solution in which an emulsifier, an antioxidant, dextrin, palm fat and oil, and trisodium phosphate are dissolved, and the solution was heated up to 85° C. Then, the solution was put together with water at 85° C. for emulsification, and was processed with a high-pressure homogenizer ("H-3-2DH" manufactured by Sanmaru Machinery Co., Ltd.) at a uniform pressure of 45 MPa to prepare an emulsified liquid. After adjusting the temperature of this emulsified liquid to 65° C., gelatin, ammonium salt, and transglutaminase were added, and a mixing and stirring treatment was performed with a kneader (manufactured by Samson Co., Ltd.) for complete dissolution. Then, 10 kg of the liquid was filled in a 10 kg packaging material, and this was packed in cardboard for molding. After gelling in a product refrigerator (10° C. or lower), an enzyme reaction was caused overnight (enzymatically crosslinked).

| | Formula tested | |
|---|---|---|
| | Comparative example | Example |
| Purified fish oil | 20.00% | 20.00% |
| Palm oil (melting point 50° C.) | 1.25% | 1.25% |
| Gelatin | 15.00% | 15.00% |
| Ammonium phosphate | 0.04% | 0.04% |
| Sucrose fatty acid ester (HLB 1) | 0.32% | 0.32% |
| Sucrose fatty acid ester (HLB 16) | 0.64% | 0.64% |
| Transglutaminase | 80 ppm | 80 ppm |
| Dextrin (DE17~21) | 3.00% | 4.00% |
| Antioxidant | 0.35% | 0.35% |
| Trisodium phosphate | 0.15% | 0.15% |
| City water | Remaining amount | |
| Total | 100.00% | |

The gel mass, which was enzymatically reacted overnight, was cut into a certain size, and coarse pulverization was performed by a production pulverizer ("QUICK MILL QMY-10" manufactured by Seishin Enterprise Co., Ltd.) with a 5 mm screen and a number of revolutions of 3470 rpm. The samples after the coarse pulverization were arranged on a tray, and by using a shelf-type freeze dryer ("DFM-10N-04" manufactured by ULVAC, Inc.), preliminary freezing was performed for 6 hours, and lyophilization was performed for 18 hours at a shelf temperature of 70° C. Each sample after lyophilization was recovered, and fine pulverization was performed by a production pulverizer ("QUICK MILL QMY-10" manufactured by Seishin Enterprise Co., Ltd.) with a 2 mm screen and a number of revolutions of 3470 rpm. In this manner, a powdered sustained-release functional material was produced. It should be noted that powders were produced with the formulation of the comparative example shown in Table 18, in the same manner, for comparison. The comparative example has a smaller formulation amount of dextrin than the example, and it has greater rupture strength and a larger rupture distortion factor.

For each of the powders of the example and the comparative example, powders that passed through a 2 mm screen were recovered, and the recovered amount, oozing of oil, and the average particle diameter of the powders was confirmed. The average particle diameter was calculated by classifying the recovered powders according to mesh sizes by a JIS test sieve. The results are shown in Table 19. The evaluation criteria for "oozing of oil" in Table 19 are as follows.
Evaluation Criteria
○: no oozing of fish oil, Δ: slight oozing of fish oil, x: oozing of fish oil

| | Formula tested | |
|---|---|---|
| | Comparative example | Example |
| Passage through 2 mm screen | 80.00% | 99.80% |
| Oozing of oil | ○ | ○ |
| Average particle diameter of powder | 724.20 μm | 655.70 μm |

As shown in Table 19, oozing of oil was not confirmed in either of the example and the comparative example. However, although the whole amount could not be recovered due to slight retention within the 2 mm screen in the comparative example where dextrin was formulated by 3%, there was no retention and nearly the whole amount could be recovered in the example where dextrin was formulated by 4%. In addition, it was confirmed that the example had a smaller average particle diameter and more fine powders than the comparative example.

Example 2

Physiologically active functional ingredients having an antioxidant function include carotenoids, and among these, astaxanthin has a particularly strong anti-oxidative power. This astaxanthin was used as the hydrophobic functional ingredient to attempt powderization. More specifically, a sustained-release functional material was produced by the same production method as Example 1 according to the formulation shown in Table 20. As a result, although emulsification occurred due to the self-emulsification ability of astaxanthin without the addition of an emulsifier, finally, powderization was enabled without the elution of oil containing astaxanthin.

| | Formula tested Example |
|---|---|
| Astaxanthin oil | 20.00% |
| Palm oil (melting point 50° C.) | 1.25% |
| Gelatin | 15.00% |
| Ammonium phosphate | 0.04% |
| Transglutaminase | 80 ppm |
| Dextrin (DE17~21) | 4.00% |
| Antioxidant | 0.25% |
| City water | Remaining amount |

Example 3

Diterpene alcohol extracted from annatto seeds is vegetable fat and oil that can become a raw material of an anti-osteoporosis agent, an anti-arteriosclerotic therapeutic agent, and the like. This diterpene alcohol was used as the hydrophobic functional ingredient to attempt powderization. More specifically, a sustained-release functional material was produced by the same production method as Example 1 according to the formulation shown in Table 21. As a result, powderization was enabled without oozing of oil.

| | Formula tested Example |
|---|---|
| Diterpene alcohol | 20.00% |
| Palm oil (melting point 50° C.) | 1.25% |
| Gelatin | 15.00% |
| Ammonium phosphate | 0.04% |
| Sucrose fatty acid ester (HLB 1) | 0.32% |
| Sucrose fatty acid ester (HLB 16) | 0.64% |
| Transglutaminase | 80 ppm |
| Dextrin (DE17~21) | 4.00% |
| Antioxidant | 0.35% |
| Trisodium phosphate | 0.15% |
| City water | Remaining amount |
| Total | 100.00% |

Example 4

Linseed oil that can be obtained from seeds of flax contains a large amount of α-linolenic acids. As in the case of DHA and EPA, α-linolenic acids have been known to exert preventive effects on coronary artery disease, stroke, and the like. In addition, this is an unsaturated fatty acid that cannot be synthesized in vivo. Therefore, it has been known that oxidation stability thereof is low, and deterioration odor/unusual odor is likely to occur. This linseed oil was used as the hydrophobic functional ingredient to attempt powderization. More specifically, a sustained-release functional material was produced by the same production method as Example 1 according to the formulation shown in Table 22. As a result, powderization was enabled without oozing of oil.

| | Formula tested Example |
|---|---|
| Linseed oil | 20.00% |
| Palm oil (melting point 50° C.) | 1.25% |
| Gelatin | 15.00% |
| Ammonium phosphate | 0.04% |
| Sucrose fatty acid ester (HLB 1) | 0.30% |
| Sucrose fatty acid ester (HLB 2) | 0.20% |
| Sucrose fatty acid ester (HLB 3) | 0.10% |
| Sucrose fatty acid ester (HLB 5) | 0.50% |
| Transglutaminase | 80 ppm |
| Dextrin (DE17~21) | 4.00% |
| Antioxidant | 0.35% |
| Trisodium phosphate | 0.15% |
| City water | Remaining amount |
| Total | 100.00% |

Example 5

Fucoxanthin, which is contained in brown seaweeds such as undaria and mekabu by a large amount, is a type of carotenoids, and it has strong anti-oxidative activity. Fucoxanthin is reported to have physiological functions such as anti-obesity, anti-diabetic, anti-angiogenic effect, and anti-tumor action. In addition, fucoxanthin is an unstable substance that is easily decomposed by heat, acid, or light stimulation. This fucoxanthin was used as the hydrophobic functional ingredient to attempt powderization. More specifically, a sustained-release functional material was produced by the same production method as Example 1 according to the formulation shown in Table 23. As a result, powderization was enabled without oozing of oil.

| | Formula tested Example |
|---|---|
| Fucoxanthin | 20.00% |
| Palm oil (melting point 50° C.) | 1.25% |
| Gelatin | 15.00% |
| Ammonium phosphate | 0.04% |
| Sucrose fatty acid ester (HLB 1) | 0.32% |
| Sucrose fatty acid ester (HLB 3) | 0.12% |
| Sucrose fatty acid ester (HLB 16) | 0.64% |
| Transglutaminase | 80 ppm |
| Dextrin (DE17~21) | 3.20% |
| Antioxidant | 0.35% |
| Trisodium phosphate | 0.15% |
| City water | Remaining amount |
| Total | 100.00% |

What is claimed is:

1. A production method of an edible sustained-release functional material, comprising:
    preparing an emulsified raw material by emulsifying fat and oil containing a hydrophobic functional ingredient;
    stirring and mixing the emulsified raw material, gelatin, transglutaminase, and dextrin having a Dextrose Equivalent value of 8 to 21;
    then forming a gel by leaving the mixture to rest; and
    after freeze-drying the gel,
    performing pulverization for powderization.

2. The production method of an edible sustained-release functional material of claim 1, wherein an emulsifier is further added at the time of the stirring and mixing.

3. The production method of an edible sustained-release functional material of claim 1, wherein ammonium salt is further added at the time of the stirring and mixing.

4. The production method of an edible sustained-release functional material of claim 1, wherein the fat and oil are fish oil containing the hydrophobic functional ingredient or hydrogenated oil in which the hydrophobic functional ingredient that is oil-soluble is dissolved.

5. The production method of an edible sustained-release functional material of claim 1, wherein the hydrophobic functional ingredient consists of DHA, EPA, astaxanthin, diterpene alcohol, linseed oil, or fucoxanthin.

6. The production method of an edible sustained-release functional material of claim 2, wherein ammonium salt is further added at the time of the stirring and mixing.

7. The production method of an edible sustained-release functional material of claim 2, wherein the fat and oil are fish oil containing the hydrophobic functional ingredient or hydrogenated oil in which the hydrophobic functional ingredient that is oil-soluble is dissolved.

8. The production method of an edible sustained-release functional material of claim 3, wherein the fat and oil are fish oil containing the hydrophobic functional ingredient or hydrogenated oil in which the hydrophobic functional ingredient that is oil-soluble is dissolved.

9. The production method of an edible sustained-release functional material of claim 6, wherein the fat and oil are fish oil containing the hydrophobic functional ingredient or hydrogenated oil in which the hydrophobic functional ingredient that is oil-soluble is dissolved.

10. The production method of an edible sustained-release functional material of claim 2, wherein the hydrophobic functional ingredient consists of DHA, EPA, astaxanthin, diterpene alcohol, linseed oil, or fucoxanthin.

11. The production method of an edible sustained-release functional material of claim 3, wherein the hydrophobic functional ingredient consists of DHA, EPA, astaxanthin, diterpene alcohol, linseed oil, or fucoxanthin.

12. The production method of an edible sustained-release functional material of claim 4, wherein the hydrophobic functional ingredient consists of DHA, EPA, astaxanthin, diterpene alcohol, linseed oil, or fucoxanthin.

13. The production method of an edible sustained-release functional material of claim 6, wherein the hydrophobic functional ingredient consists of DHA, EPA, astaxanthin, diterpene alcohol, linseed oil, or fucoxanthin.

14. The production method of an edible sustained-release functional material of claim 7, wherein the hydrophobic functional ingredient consists of DHA, EPA, astaxanthin, diterpene alcohol, linseed oil, or fucoxanthin.

15. The production method of an edible sustained-release functional material of claim 8, wherein the hydrophobic functional ingredient consists of DHA, EPA, astaxanthin, diterpene alcohol, linseed oil, or fucoxanthin.

16. The production method of an edible sustained-release functional material of claim 9, wherein the hydrophobic functional ingredient consists of DHA, EPA, astaxanthin, diterpene alcohol, linseed oil, or fucoxanthin.

* * * * *